United States Patent [19]

Franz et al.

[11]  4,195,983

[45]  Apr. 1, 1980

[54] N-TRIFLUOROACETYL-N-PHOSPHINO-THIOYLMETHYLGLYCINE ESTERS

[75] Inventors: John E. Franz, Crestwood; Robert J. Kaufman, University City, both of Mo.

[73] Assignee: Monsanto Company, St. Louis, Mo.

[21] Appl. No.: 973,317

[22] Filed: Dec. 26, 1978

[51] Int. Cl.$^2$ ............................ A01N 9/36; C07F 9/40
[52] U.S. Cl. ........................................ 71/87; 260/941
[58] Field of Search ............................ 260/941; 71/87

[56]  References Cited

U.S. PATENT DOCUMENTS

| | | | |
|---|---|---|---|
| 3,799,758 | 3/1974 | Franz | 71/86 |
| 3,991,095 | 11/1976 | Gaertner | 71/86 |

OTHER PUBLICATIONS

Rueppel et al., "Biomedical Mass Spectrometry", vol. 3, (1976), pp. 28-31.

*Primary Examiner*—Anton H. Sutto
*Attorney, Agent, or Firm*—William T. Black; Donald W. Peterson

[57]  ABSTRACT

This invention relates to a new class of organic chemical compounds. More particularly, this invention is concerned with ester derivatives of N-trifluoroacetyl-N-phosphinothioylmethylglycine. This class of compounds has been found to be useful as intermediates in producing N-phosphinothioylmethylglycine esters which show herbicidal activity. Some of the class of compounds of this invention also show herbicidal activity when applied to certain varieties of weeds or undesired plants.

7 Claims, No Drawings

N-TRIFLUOROACETYL-N-PHOSPHINOTHIOYL-METHYLGLYCINE ESTERS

This invention relates to a new class of organic chemical compounds. More particularly, this invention is concerned with ester derivatives of N-trifluoroacetyl-N-phosphinothioylmethylglycine wherein ester or thioester groups are bonded to the phosphorus atom in addition to a divalent sulfur atom. This class of compounds has been found to display desirable herbicidal activity when applied to certain varieties of weeds or undesired plants.

U.S. Pat. No. 3,799,758 describes the preparation of N-phosphonomethylglycine and certain of its esters, amides and salts. Also described is the use of such compounds as contact or post-emergent herbicides.

U.S. Pat. No. 3,991,095 describes derivatives of N-phosphonomethylglycine and salts thereof wherein there is a thiocarbonyl group attached to the nitrogen atom.

*Biomedical Mass Spectrometry*, Vol. 3, (1976) pages 28–31 describes the tributyl ester derivatives of N-trifluoroacetyl-N-phosphonomethylglycine.

It will be apparent from a study of the above patents and publication that none of them disclose or suggest N-trifluoroacetyl-N-phosphonomethylglycines containing a P=S grouping.

The compounds of the present invention are represented by the formula

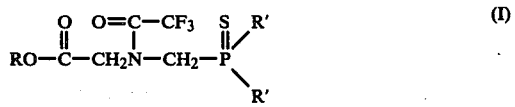

wherein R is a member of the class consisting of alkyl of from 1 to 10 carbon atoms, chloroalkyl of from 1 to 4 carbon atoms and from 1 to 3 chlorine atoms and alkoxyalkyl containing from 3 to 7 carbon atoms and each R' is a member of the class consisting of thioalkyl or alkoxy of from 1 to 6 carbon atoms, cyanoalkoxy, chloroalkenyloxy, phenoxy, phenylthio and substituted phenoxy and phenylthio having 1 to 2 substituents selected from the class consisting of halo, trifluoromethyl, lower alkyl and lower alkoxy. It is preferred that R be alkyl or chloroalkyl of from 1 to 4 carbon atoms. It is even more preferred that R be methyl or ethyl. It is preferred that R' represent phenylthio, phenoxy or alkylthio of from 1 to 4 carbon atoms. It is even more preferred that R' represent alkylthio of from 1 to 4 carbon atoms.

Illustrative of the alkyl groups represented by R are methyl, ethyl, n- and isopropyl, n-, sec, iso- and tert-butyl, pentyl, hexyl, octyl and decyl. The chloroalkyl groups that R represents are, for example, chloromethyl, chloroethyl, chloropropyl, trichloropropyl, chlorobutyl and the like.

Illustrative of the alkoxyalkyl groups which R represents are methoxyethyl, methoxypropyl, methoxybutyl, ethoxyethyl, ethoxypropyl, propoxyethyl, propoxypropyl and the like.

The substituted phenoxy and phenylthio groups which R' represents are, for example, halogen-substituted groups such as chlorophenoxy, bromophenoxy, iodophenylthio, fluorophenylthio, dichlorophenylthio, dibromophenylthio, chlorobromophenoxy and the like, tolyoxy, ethylphenylthio, butylphenylthio, methoxyphenylthio, methylchlorophenoxy, ethylbromophenylthio, ethoxyphenylthio, butoxyphenoxy, and the like.

In accordance with the present invention, the compounds of formula (I) are prepared by reacting a compound of the formula

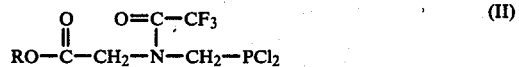

wherein R is as above defined with an alcohol or thiol of the formula

R'—Z—H wherein R' is as above defined and Z is oxygen or sulfur, in the presence of a hydrogen halide acceptor and then treating the reaction mixture with at least an equivalent amount of elemental sulfur.

The above reaction is generally conducted at ambient temperature. However, temperatures in the range of from 0° C. to 50° C. can be employed. Ambient temperatures of from 15° C. to 25° C. are preferred for convenience.

If it is desired to produce compounds of formula (I) wherein each R' is different, it is necessary to perform sequential steps of esterification with the hydrogen halide acceptor. In each instance, one equivalent of the compound of the formula

R'—Z—H wherein R' and Z are as above defined is added at each step.

It is, of course, apparent to those skilled in the art that for each chloro group in the compounds of formula (II) one should employ at least one equivalent of the alcohol or thioalcohol of formula (II) together with at least an equivalent amount of the hydrogen halide acceptor.

Inasmuch as the dichlorophosphinyl compounds of formula (II) are unstable towards moisture, the reaction, for best results, must be conducted in an anhydrous environment, that is, anhydrous reagents and solvents should be employed. Although the reaction can be conducted in a stepwise manner, i.e., by isolating the dichloro compound of formula (II) and then conducting the esterification and then subsequent conversion to the thioyl derivative, it is preferred for convenience to conduct the total reaction in a single reaction vessel without complete isolation and identification of the dichlorophosphinic compound.

The starting materials employed in the production of the compounds of the invention are prepared by the following general procedure.

An ester of N-hydroxyphosphinylmethylglycine is dissolved in trifluoroacetic acid and an equal molar quantity or slight excess of trifluoroacetic anhydride is added dropwise with stirring at ambient temperature. Too large an excess of anhydride should be avoided to obtain the best yields of the compound. The reaction mixture is then concentrated in vacuo to yield the ester of N-trifluoroacetyl-N-(hydroxyphosphinylmethyl)glycine.

The ester of N-trifluoroacetyl-N-(hydroxyphosphinylmethyl)glycine is then converted to the ester of N-trifluoroacetyl-N-[bis(chloro)phosphonomethyl]glycine by dissolving in benzene and then adding excess phosphorus trichloride at ambient temperature. The phosphine dichloride is recovered by filtration and then concentration of the filtrate in vacuo.

The dichloro phosphine compound is extremely sensitive to moisture. It is, therefore, desirable and necessary to employ anhydrous reagents and aprotic solvents while protecting the reaction mixture from moisture to obtain the best yields.

The compounds of this invention are useful as herbicides or as intermediates in the preparation of herbicides, e.g., the trifluoroacetyl group can be removed by treating the compounds of the invention with sodium tetrahydridoboron in a solvent such as ethanol.

The following examples serve to further illustrate the invention. In the examples, all parts are parts by weight unless otherwise expressly set forth.

EXAMPLE 1

2-Ethoxyethyl-N-(trifluoroacetyl)-N-(hydroxyphosphinylmethyl)glycine was converted to 2-ethoxyethyl-N-(trifluoroacetyl)-N-[bis(chloro)phosphinomethyl]glycine by dissolving in benzene and dropwise addition to a stirred solution of excess phosphorus trichloride. After stirring for five to ten minutes, the turbid solution was filtered and concentrated in vacuo to yield the phosphine dichloride (6.2 g., 0.01731 mole). The phosphine dichloride was dissolved in tetrahydrofuran. To this solution was added dropwise with stirring ethanol (1.592 g.) and triethylamine (3.48 g.) dissolved in 50 ml. of tetrahydrofuran. The reaction mixture was stirred for an additional two hours and sulfur (0.554 g., 0.01731 mole) was added and stirring continued overnight. The reaction mixture was filtered, concentrated to dryness and the residue dissolved in diethyl ether. The diethyl ether solution was then washed with 5% aqueous hydrochloric acid, 5% aqueous sodium bicarbonate and then dried over magnesium sulfate. The ethereal solution was then filtered and concentrated in vacuo to yield a residue. This residue was dissolved in methanol, centrifuged to remove any unreacted sulfur and the supernatant methanol solution decanted and concentrated to dryness. This residue was chromatographed on silica gel employing dichloromethane as the solvent to yield 2-ethoxyethyl-N-(trifluoroacetyl)-N-[bis(ethoxy)phosphinothioylmethyl]glycine (0.9 g.) as an oil, $N_D^{25}=1.4696$ and having the following analysis.

Calc'd: C, 38.14; H, 5.66; N, 3.42. Found: C, 37.69; H, 5.65; N, 3.44.

EXAMPLE 2

Ethyl-N-(hydroxyphosphinylmethyl)-N-(trifluoroacetyl)glycinate (2.8 g.) was dissolved in benzene and added dropwise to excess phosphorus trichloride with stirring. The solution was filtered and the supernatant liquid decanted and evaporated under vacuum to yield ethyl-N-(trifluoroacetyl)-N-[bis(chloro)phosphinomethyl]glycine as a clear oil. The clear oil was dissolved in tetrahydrofuran and a solution of methane thiol (0.96 g.) and triethylamine (2.05 g.) dissolved in tetrahydrofuran added with stirring. After stirring for an additional one hour, sulfur (0.32 g.) was added and the solution stirred overnight. The reaction mixture was then filtered and the solvent removed under vacuum. The residue was chromatographed on silica gel employing dichloromethane to yield ethyl-N-(trifluoroacetyl)-N-[bis(methanethio)phosphinothioylmethyl]glycine as an oil, $N_D^{25}=1.5132$ and having the following analysis.

Calc'd: C, 29,26; H, 4.04; N, 3.79. Found: C, 29.55; H, 4.32; N, 3.26.

EXAMPLE 3

Ethyl-N-(trifluoroacetyl)-N-(hydroxyphosphinylmethyl)glycine (2 g., 0.0072 mole) was converted to ethyl-N-(trifluoroacetyl)-N-[bis(chloro)phosphinomethyl]glycine as in the previous example. The resulting dichlorophosphine was dissolved in tetrahydrofuran and a solution of m-trifluoromethylphenol (2.3 g.) and triethylamine (1.46 g.) dissolved in tetrahydrofuran was added dropwise with stirring. After one and a half hours, sulfur (0.234 g.) was added and the reaction stirred overnight. The reaction mixture was then filtered, concentrated in vacuo, extracted with petroleum ether and concentrated to dryness. The residue was chromatographed on silica gel employing methylene chloride to yield ethyl-N-(trifluoroacetyl)-N-[bis-(m-trifluoromethylphenoxy)phosphinothioylmethyl]]glycine as a clear oil, $N_D^{25}=1.4715$ and having the following analysis.

Calc'd: N, 2.34; S, 5.37. 1 Found: N, 2.39; S, 5.26.

EXAMPLE 4

Ethyl-N-(trifluoroacetyl)-N-(hydroxyphosphinylmethyl)glycine was converted to ethyl-N-(trifluoroacetyl)-N-[bis(chloro)phosphinomethyl]glycine with phosphorus trichloride as in Example 2. The phosphine dichloride (0.8 g.) was dissolved in tetrahydrofuran (10 ml.) and a solution of n-butane thiol (0.5 g.) and triethylamine (0.5 g.) dissolved in tetrahydrofuran was added dropwise with stirring. Sulfur (8.08 g.) was then added and the reaction stirred for one hour. The reaction mixture was then filtered, concentrated in vacuo, extracted with boiling petroleum ether and the petroleum ether solution concentrated to dryness. The residue was chromatographed on silica gel using a 40% volume mixture of dichloromethane in cyclohexane to yield ethyl-N-(trifluoroacetyl)-N-[bis(n-butylthio)phosphinothioylmethyl]glycine as an oil, $N_D^{25}=1.5102$ and having the following analysis.

Calc'd: N, 3.09; P, 6.83; S, 21.21. Found: N, 3.31; P, 6.75; S, 20.94.

EXAMPLE 5

Ethyl-N-(trifluoroacetyl)-N-(hydroxyphosphinylmethyl)glycine (4 g.) was converted to its phosphine dichloride derivative as in Example 2. The dichloride derivative was then dissolved in tetrahydrofuran and isopropanol (1.728 g., 0.0290 mole) and triethylamine (2.92 g., 0.0290 mole) dissolved in tetrahydrofuran were added dropwise with stirring. The mixture was stirred for two hours and sulfur (0.463 g., 0.0145 mole) was added. The mixture was stirred overnight and the reaction filtered, concentrated in vacuo, dissolved in diethyl ether and washed with 5% aqueous hydrochloric acid and then 5% aqueous sodium bicarbonate. The ethereal solution was dried over magnesium sulfate, filtered and then concentrated in vacuo to yield an oily residue. The oily residue was chromatographed on silica gel with dichloromethane to yield ethyl-N-(trifluoroacetyl)N-[bis(2-propoxy)phosphinothioylmethyl]glycine (1.8 g.) as a yellow oil, $N_D^{25}=1.555$ and having the following analysis.

Calc'd: C, 39.69; H, 5.89; N, 3.56; P, 7.87. Found: C, 39.86; H, 6.01; N, 3.70; P, 7.60.

EXAMPLE 6

Ethyl-N-(trifluoroacetyl)-N-(hydroxyphosphinylmethyl)glycine (4 g.) was converted into the phosphine dichloride as in Example 2. The dichloride was dissolved in tetrahydrofuran and a solution of triethylamine (2.93 g., 0.0290 mole) and 2-cyano ethanol (2.061 g., 0.0290 mole) was added dropwise with stirring. After stirring for one hour, sulfur (0.463 g., 0.0145 mole) was added and the solution stirred overnight. The solution was then filtered, concentrated to dryness and dissolved in dichloromethane. The dichloromethane solution was washed with 5% aqueous hydrochloric acid and then 5% aqueous sodium bicarbonate and dried over magnesium sulfate. The dichloromethane solution was then filtered and concentrated to dryness to yield an oily residue. The oily residue was chromatographed on silica gel using 25% acetonitrile in diethyl ether (v:v) to yield ethyl-N-(trifluoroacetyl)-N-[bis(2-cyanoethoxy)-phosphinothioylmethyl]glycine as a yellow oil, $N_D^{25} = 1.4734$ and having the following analysis.

Calc'd: C, 37.59; H, 4.13; N, 10.12; P, 7.46; S, 7.72. Found: C, 37.74; H, 4.20; N, 9.93; P, 7.30; S, 7.64.

EXAMPLE 7

Ethyl-N-(trifluoroacetyl)-N-(hydroxyphosphinylmethyl)glycine (2 g., 0.0072 mole) was converted to its phosphine dichloride as in Example 2. The phosphine dichloride was dissolved in tetrahydrofuran and a solution of 2-chloroallyl alcohol (1.33 g.) and triethylamine (2 g.) dissolved in tetrahydrofuran was added dropwise with stirring. After stirring for 2 hours, sulfur (0.234 g.) was added and the solution stirred overnight. The solution was filtered and concentrated in vacuo to yield an oily residue. The oily residue was extracted into petroleum ether and concentrated in vacuo to yield ethyl-N-(trifluoroacetyl)-N-[bis(2-chloroallkloxy)phosphinothioylmethyl]glycine (1.9 g.) as a clear oil, $N_D^{25} = 1.457$ and having the following analysis.

Calc'd: C, 34.08; H, 3.74; N, 3.06; S, 7.00. Found: C, 34.11; H, 3.90; N, 3.27; S, 6.84.

EXAMPLE 8

Ethyl-N-(trifluoroacetyl)-N-[bis(chloro)phosphinomethyl]glycine was prepared as in Example 2. The dichloro phosphine (0.8 g.) was dissolved in diethyl ether (10 ml.) and a solution of phenol (0.470 g.) and triethylamine (0.510 g.) dissolved in diethyl ether was added dropwise with stirring. The reaction mixture was stirred for two hours and then sulfur (0.08 g.) was added and the reaction stirred for an additional two hours. The reaction mixture was then centrifuged. The precipitated solid was washed with diethyl ether and the washed diethyl ether was added to the original supernatant diethyl ether solution and evaporated to dryness under vacuum to yield an oily residue. The oily residue was then extracted with boiling petroleum ether and concentrated to dryness to yield ethyl-N-(trifluoroacetyl)-N-[bis(phenoxy)phosphinothioylmethyl]glycine as a water white oil, $N_D^{25} = 1.5430$ and having the following analysis.

Calc'd: C, 49.46; H, 4.15; P, 6.71; S, 6.95. Found: C, 49.31; H, 4.09; P, 6.58; S, 7.03.

EXAMPLE 9

Ethyl-N-(trifluoroacetyl)-N-[bis(chloro)phosphinomethyl]glycine was prepared as in Example 2. The phosphine dichloride (0.83 g.) was dissolved in diethyl ether (10 ml.) and benzene thiol (0.58 g.) and triethylamine (0.51 g.) dissolved in 10 ml. of diethyl ether was added with stirring. The reaction mixture was stirred for an additional two hours and sulfur (0.083 g.) was added and stirring continued for several hours. The reaction mixture was then centrifuged and the precipitate washed with 20 ml. of diethyl ether. The diethyl ether washings were combined with the diethyl ether supernatant liquid from the centrifugation and the diethyl ether solution concentrated to dryness to yield a residue. This residue was extracted with boiling petroleum ether and then concentrated in vacuo to yield an oil which was chromatographed on silica gel employing dichloromethane to yield ethyl-N-(trifluoroacetyl)-N-[bis(thiophenoxy)phosphinothioylmethyl]glycine as an oil, $N_D^{25} = 1.4931$ and having the following analysis.

Calc'd: C, 46.25; H, 4.02; N, 2.84; P, 6.29. Found: C, 46.39; H, 4.10; N, 2.77; P, 6.40.

EXAMPLE 10

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules of the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the table. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the table under WAT and the results recorded. In some instances, the four-week observations are omitted.

The post-emergence herbicidal activity index used in Table I is as follows:

| Plant Response | Index |
|---|---|
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| A - Canada Thistle* | G - Yellow Nutsedge* |
| --- | --- |
| B - Cocklebur | H - Quackgrass* |
| C - Velvetleaf | I - Johnsongrass* |
| D - Morningglory | J - Downy Brome |
| E - Lambsquarters | K - Barnyardgrass |
| F - Smartweed | |

*Established from vegetative propagules.

Table I

| Compound of Example No. | WAT | Kg/h | Post-Emergent Plant Species | | | | | | | | | | |
| --- | --- | --- | --- | --- | --- | --- | --- | --- | --- | --- | --- | --- | --- |
| | | | A | B | C | D | E | F | G | H | I | J | K |
| 1 | 2 | 11.2 | 0 | 0 | 0 | 0 | 1 | 0 | 0 | 0 | 0 | 0 | 0 |
| 1 | 2 | 5.6 | 0 | 0 | 0 | 0 | 1 | 0 | 0 | 0 | 0 | 0 | 0 |
| 2 | 4 | 11.2 | 4 | 2 | 4 | 2 | 3 | 2 | 3 | 2 | 3 | 2 | 3 |
| 2 | 4 | 5.6 | 1 | 2 | 1 | 1 | 1 | 2 | 1 | 3 | 3 | 2 | 3 |
| 3 | 4 | 11.2 | 1 | 1 | 1 | 1 | 2 | 1 | 2 | 2 | 2 | 2 | 2 |
| 4 | 4 | 11.2 | 1 | 2 | 1 | 2 | 3 | 1 | 2 | 2 | 2 | 2 | 3 |
| 4 | 2 | 5.6 | 0 | 1 | 0 | 1 | 1 | 0 | 1 | 0 | 0 | 0 | 1 |
| 5 | 4 | 11.2 | 0 | 0 | 0 | 1 | 4 | 1 | 0 | 0 | 0 | 0 | 1 |
| 5 | 2 | 5.6 | 0 | 0 | 0 | 0 | 0 | 0 | 0 | 0 | 0 | 0 | 1 |
| 6 | 2 | 11.2 | 0 | 0 | 0 | 1 | 0 | 0 | 0 | 0 | 0 | 0 | 0 |
| 6 | 2 | 5.6 | 0 | 0 | 0 | 1 | 0 | 0 | 0 | 0 | 0 | 0 | 0 |
| 7 | 2 | 11.2 | 0 | 0 | 0 | 0 | 0 | 0 | 0 | 0 | 0 | 0 | 0 |
| 7 | 2 | 5.6 | 0 | 0 | 0 | 0 | 0 | 0 | 0 | 0 | 0 | 0 | 0 |
| 8 | 2 | 11.2 | 0 | 0 | 0 | 0 | 0 | 0 | 0 | 0 | 0 | 0 | 0 |
| 8 | 2 | 5.6 | 0 | 0 | 0 | 0 | 0 | 0 | 0 | 0 | 0 | 0 | 0 |

From the test results presented in Table I, it can be seen that the post-emergent herbicidal activity of the compounds of this invention is, for the most part, general in nature. In certain specific instances, however, some selectivity is demonstrated. In this regard, it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. When required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent," it is understood that wetting agents, dispersing agent, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 22.4 or more kilograms per hectare. In pre-emergent treatments, the rate of application can be from about 11.2 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this application, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

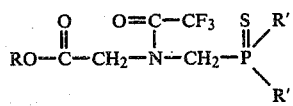

wherein R is a member of the group consisting of alkyl of from 1 to 10 carbon atoms, chloroalkyl of from 1 to 4 carbon atoms and from 1 to 3 chlorine atoms and alkoxyalkyl containing from 3 to 7 carbon atoms and each R' is a member of the class consisting of thioalkyl or alkoxy of from 1 to 6 carbon atoms, cyanoalkoxy, chloroalkenyloxy, phenoxy, phenylthio and substituted phenoxy and phenylthio having 1 to 2 substituents selected from the class consisting of halo, trifluoromethyl, lower alkyl and lower alkoxy.

2. A compound of claim 1 wherein R is alkyl of from 1 to 4 carbon atoms.
3. A compound of claim 1 wherein R is ethyl.
4. A compound of claim 3 wherein R' is methylthio.
5. A compound of claim 3 wherein R' is m-trifluoromethylphenoxy.
6. A compound of claim 3 which is butylthio.
7. A herbicidal composition comprising a herbicidally effective amount of a compound of claim 1 and an inert diluent.

* * * * *